US011643641B2

(12) United States Patent
Reddy

(10) Patent No.: US 11,643,641 B2
(45) Date of Patent: May 9, 2023

(54) PREVENTION OF VIRAL TRANSMISSION BY NAKED GENETIC MATERIAL

(71) Applicant: Malireddy S. Reddy, Cherry Hills Village, CO (US)

(72) Inventor: Malireddy S. Reddy, Cherry Hills Village, CO (US)

( * ) Notice: Subject to any disclaimer, the term of this patent is extended or adjusted under 35 U.S.C. 154(b) by 0 days.

(21) Appl. No.: 17/681,206

(22) Filed: Feb. 25, 2022

(65) Prior Publication Data

US 2022/0282224 A1  Sep. 8, 2022

Related U.S. Application Data

(60) Provisional application No. 63/156,878, filed on Mar. 4, 2021.

(51) Int. Cl.
*C12N 7/00* (2006.01)

(52) U.S. Cl.
CPC ...... *C12N 7/00* (2013.01); *C12N 2770/20063* (2013.01)

(58) Field of Classification Search
None
See application file for complete search history.

(56) References Cited

U.S. PATENT DOCUMENTS

| 10,188,732 B2 | 1/2019 | Conley et al. | |
|---|---|---|---|
| 2009/0176681 A1* | 7/2009 | Kaneda | C11D 3/222 510/311 |
| 2011/0070306 A1* | 3/2011 | Baker, Jr. | A61K 31/522 514/263.37 |
| 2017/0044468 A1* | 2/2017 | Gori | C11D 3/33 |
| 2017/0355930 A1* | 12/2017 | Lant | C11D 1/146 |

OTHER PUBLICATIONS

"Many common household cleaning products can kill the coronavirus if you use them properly" By Herb Weisbaum, Updated Apr. 24, 2020 retrieved from https://www.nbcnews.com/better/lifestyle/many-common-household-cleaning-products-can-kill-coronavirus-if-you-ncna1160271 (Year: 2020).*
Leclercq et al. et al., European Journal of Pharmaceutical Sciences, 155:105559 (Year: 2020).*
CDC, Recommendations of CDC and the Healthcare Infection Control Practices Advisory Committee (HICPAC) from https://www.cdc.gov/infectioncontrol/pdf/guidelines/environmental-guidelines-P.pdf (18 page selection) (Year: 2019).*

* cited by examiner

Primary Examiner — Shanon A. Foley
Assistant Examiner — Myron G Hill
(74) Attorney, Agent, or Firm — Kyle W. Rost

(57) ABSTRACT

A method and composition for inactivating both naked genetic material such as RNA and DNA and inactivating mechanical delivery vectors in a treatment space external of the human body. To practice the method, apply a mist of lipid molecule degrading agent effective against viral membranes with lipid molecules. Then apply an inactivator of spike proteins and other viral residues. Next, reduce the threat of transmitting genetic material by applying inactivators of mechanical transport vectors such as mold, yeast, and bacteria. Further, pretreat the treating space to receive enzymatic agents by applying a surface detoxifying agent in quantity sufficient to inactivate substances detrimental to enzymes that break the naked viral genetic material. Then, apply preparatory enzymes that degrade microorganisms and their cellular components. Finally, apply enzymes for breaking the naked viral genetic material, as present.

7 Claims, 2 Drawing Sheets

DEGRADE LIPIDS — 12

INACTIVATE SPIKE PROTEINS — 16

INACTIVATE MECHANICAL VECTORS — 20

DETOXIFY — 24

REDUCE CARRIERS — 30

RNA-ASE DNA-ASE — 34

Fig. 1

PREVENTION OF VIRAL TRANSMISSION BY NAKED GENETIC MATERIAL

BACKGROUND OF THE INVENTION

Field of the Invention

The invention relates to methods or apparatus for disinfecting or sterilizing materials or objects. Processes and devices are used to administer multistage biocidal treatment. The invention also relates to preparations for medical purposes, and to devices or methods specially adapted for bringing pharmaceutical products into particular physical forms for disinfection or sterilization.

Description of Related Art Including Information Disclosed Under 37 CFR 1.97 and 1.98

Coronaviruses are a large group of enveloped single strand, positive sense RNA viruses. The SARS-CoV-2 viral RNA behaves like MRNA, makes proteins through translation, replicates to form several RNA strands, and gets assembled into multiple virus particles in a host cell. Most of the human coronaviruses belong to the genera Beta coronavirus, including SARS-CoV, MERS-CoV, and SARS-CoV-2.

The diameter of the spherical virus with extensive pleomorphism varies from 60 to 140 nanometers. The number of spikes on coronavirus is predicted to be around 90 per viral particle. The length of the spike is around 9 to 10 nanometers. Assuming the diameter of the COVID-19 virus is 100 nanometers, the length of each spike is roughly 10% of the diameter of the intact viral particle. Due to the presence of close to 90 spikes on each viral particle, the adhesion rate of the COVID-19 coronavirus to stick to ACE-2 receptor sites of a host human body is significantly high. The latest SARS-CoV-2 mutants that were isolated and confirmed to cause COVID-19 disease in humans had 70% more infective properties than the original novel SARS-CoV-2 virus, implying that either the number of spike proteins is more or the composition of the spike proteins is such that they have more adhesion properties than the parent strain. It has been confirmed that viral mutations since September 2020 take place in the spike proteins. One can hypothesize that the parent SAS-CoV-2 virus has not been stable outside the human body, perhaps due to loss of the spike proteins or due to damage to the envelope with the lipid fractions. This instability results in a tendency for the virus to mutate.

Apparently the virus is mutating in the human cell through alteration of the amino acid sequence of the spike protein, through increase in number of spikes, or through modification of the lipid containing envelope layer composition to further strengthen integrity. Current vaccines are aimed at producing antibodies to the original parent viral spike proteins. The mutation involving the spike proteins may alter the effectiveness of a vaccine to the point of making the vaccine non-functional or of significantly reduced function in protecting the human host. In this regard, it appears that the necessity for the virus to mutate so suddenly is because of damaged, naked RNA being introduced into the human cell through mechanical vectors. Thus, the naked viral genome—RNA—introduced into the human cell is further mutating, which may result in strengthening. This is entirely possible because the naked RNA of the coronavirus genome is 30 kilobases of RNA, which is the amount of RNA contained in a virus. Also, the SARS-CoV-2 viral RNA is linear and has 10 to 14 open reading frames (ORF). These 14 ORFs will encode for 27 proteins. In addition, the coronavirus genome (RNA) can code for several accessory proteins that are not essential for replication. In this connection, 1 kilobase (kb) is equivalent to 1000 kbs. In a simplified way, SARS-CoV-2 RNA will have roughly 30,000 kbs (nucleotides). Thus, naked RNA of coronavirus with 30,000 kbs, or even less due to damage, when introduced into the human cell through mechanical vectors, will have more chances to mutate due to lack of certain essential factors such as enzymes, through both antigenic shift and antigenic drift. Thus, it appears that naked RNA introduced into the human cell with the aid of mechanical vectors has more chances to mutate than does either the RNA of the intact viral particle introduced through the aid of spikes or viral membrane introduced into the human cell membrane.

The coronavirus can enter into the human cell within 15 minutes of contact. The eclipse period is defined as the time from entry into the cell to the release of newly formed viruses. For the coronavirus, this eclipse period is roughly 12-36 hours. If all the ingredients and viral structures are intact, the viral multiplication and the eclipse period can be as little as 12 hours. If the virus genome is altered or perhaps introduced as naked RNA by a mechanical vector, the eclipse period might be longer than 36 hours. The longer the eclipse period, the greater the chance for viral mutation. It appears that naked RNA introduced into a partially injured human cell, as with a comorbid condition, needs a longer eclipse period and will have more chance to mutate, perhaps due to lack of some of the essential enzymes or other unknown factors associated with an intact viral particle.

The burst size is defined as the number of virus particles produced from each infection of one corona viral particle in one human cell. The burst size in SARS-CoV-2 virus is roughly 600 to 700 virus particles. In simple terms, the number of viral particles that each one coronavirus can replicate and produce within a human cell in roughly 36 hours is approximately 600 to 700. In the case of naked RNA introduced into a human cell, the burst size may be the same. The disease duration of COVID-19, which is the median time from onset to clinical recovery from a mild case, is approximately 2 weeks. For patients with a severe or critical disease, the disease duration is 3-6 weeks. Where the patient is infected with naked RNA, the disease duration could be longer because of a longer eclipse period, longer latent period, and larger burst size. The pathogenesis by naked RNA of SARS-CoV-2 coronavirus cannot be ignored, specifically when considering viral mutations.

Coronavirus, including SARS-CoV-2 virus, cannot replicate within the infected cell cytoplasm without the assistance of the host machine, fortunately making integration of virus genome into the host cell chromosome not so likely. Coronaviruses have the largest RNA genome among RNA viruses and thus have room for the insertion of large foreign genes, to amplify the rate of mutation due to recombination.

Generally, viruses are continuously changing as a result of genetic selection. They undergo subtle genetic changes through mutation, and major genetic changes through recombination. Mutation occurs when an error is incorporated in the viral genome. Recombination occurs when co-infecting viruses exchange genetic information, creating a novel virus.

The mutation rate of DNA viruses (but not coronaviruses) is approximately that of eucaryotic cells, in theory yielding one mutant virus in from several hundred to many thousand per virus genome copy, which is significantly low. Examples for DNA virus are smallpox and herpes. RNA viruses, such as SARS-CoV-2 coronavirus, have much higher mutation rates, perhaps one mutation per virus genome copy, which is significantly high due to their RNA dependent RNA polymerase enzyme lacks the proof reading ability to prevent the mutations. Thus, mutations can produce viruses with new antigenic determinants.

Antigenic drift and antigenic shift are two contrasting terms that describe significantly different versions of viral mutation. Antigenic drift is the accumulation of a series of minor genetic mutations in genes of the same virus. Viral mutants due to antigenic drift develop slowly over a time. The mutated strain is somewhat similar to the parent strain, infects only the same human species, and is non-zoonotic. Thus, mutated viruses due to antigenic drift are species specific and do not cross the species barrier.

Alterations in the genetic material of a virus by antigenic drift lead to changes in the function of viral proteins. Such changes result in the creation of new viral strain of altered acute virulence in comparison to the parent, and unfortunately this occurs frequently. However, such new viral strain is species specific, like its parent. An example of viral infection due to antigenic drift is influenza H3N2 variant in 2003-2004 flu season, which was responsible for severe infections and lasted for a longer period than any other past flu season. This is the main reason for the failure to develop a 100% effective influenza vaccine, and consequently a new modified vaccine has to be developed every year prior to the flu season.

Antigenic shift is an intermixing of genes of several viruses, typically in the infected eucaryotic cell, from a wide range of viruses that may be capable of infecting both humans and animals. This occurs when two genetically different viruses combine to form a new virus with a new sub-type or mix of genes including some from an animal population, as in the case in 2009 of a new H1N1 virus that had a combination of genes from pigs, birds, and humans. Thus, the appearance of an antigenically novel virus, a new sub-type, through recombination and subsequent mutation is by antigenic shift. The mixing of genes may include influenza viruses. The resulting new viruses are zoonotic, spreading between animals and humans. Antigenically altered novel viruses may be able to cause diseases in previously resistant or immune hosts. The major changes due to antigenic shift happen suddenly enough that the human immune system may not recognize the novel virus. This may describe a current situation with COVID-19 pandemic.

Recombination describes the exchange of genetic material between two viruses during co-infection of a host cell. The current SARS-CoV-2 virus may once again gain or exchange genes from other influenza viruses or any other RNA viruses, resulting in a new sub-type with much higher pathogenicity, which can infect both humans and animals. However, fortunately so far mutation due to antigenic shift is not frequent.

A classic example of antigenic shift is the H1N1 influenza virus strain. The avian H1N1 strain mutation, responsible for the 1918 pandemic, caused 50 to 100 million human deaths. The same virus also caused pandemics in 1934 and 1947. The reappearance of a virus strain after a long absence is believed to be the result of a recombination event involving the independent assortment of genes from two variant viruses rather than from antigenic drift due to alteration of genetic material of the parent strain.

When a coronavirus enters into a host cell and is simultaneously co-infected by any other virus, the result can be a new virus with higher pathogenicity. It can infect people who were resistant to the parent coronavirus and lead to an uncontrollable pandemic. Thus, coronavirus SARS-CoV-2 can mutate once again through a series of antigenic drifts, antigenic shifts, or both and cause a future pandemic. There has been worldwide concern over the possibility of such mutation, especially in view of future flu seasons expected to arrive while the COVID-19 pandemic remains active.

When outside the human body, coronaviruses experience changes in their morphology to make them less infective or totally non-infective. The main genetic determinant of SARS-CoV-2, like any other coronavirus, is its single strand RNA. When an intact SARS-CoV-2 virus is outside the human body, which constitutes an adverse condition for the virus, it may start to lose some of its structural components such as S (spike protein) and other proteins like M (membrane), N (nucleocapsid), E (envelope) and the protective lipid containing layer of the envelope. These loses are by disintegration of the viral particle. RNA normally is enveloped and protected by the viral nucleocapsid, but under adverse conditions, the RNA will be liberated from the integral virus structure. Such an exposed viral RNA is scientifically termed naked RNA. Stripped from the structured viral particle, naked RNA continues to have functional capability for a limited time. There is concern that naked RNA with functional genetic determinants, i.e. viral genes, continues to have an ability to infect a susceptible human cell even without the aid of spike proteins and a protective layer. It has been projected that intact COVID-19 virus becomes ineffective after it has been outside the human body for as little as 72 hours and at the most one week. However, similar projection has not been offered about the infective capacity of naked RNA.

Commonly, the coronavirus functions to infect a host human cell using its spike proteins (S), followed by integration of its membrane into the host cell membrane, thus gaining entrance into cell cytoplasm to release its RNA to replicate and produce more infective viral particles and thus destroy further host cells and tissue and continue the infection. However, under the adverse condition of being outside the human body, the COVID-19 virus starts losing surface viral proteins and protective membranes, which are essential for viral survival, adsorption and penetration into the human cell. With these loses, it is deemed that the virus has lost its ability to infect. However, it appears the functional naked RNA remains intact and would have the capacity to replicate in human cells if introduced through a mechanical vector. A similar mechanism may exist with naked DNA of the infective DNA viruses.

When it integrates with silica, naked RNA of the coronavirus of MERS-CoV is known to stay intact for up to sixteen weeks, even at room temperature. The silica can be the common component of dust, readily found almost everywhere. It is a concern that viral, naked RNA can become stabilized at room temperature using a silica membrane. If naked RNA of coronavirus adheres to fine silica and mold hyphae, whether alive or dead, it then might enter nasopharyngeal orifices. Inflammation started by the mold hyphae and inflammation due to secondary pathogenic bacterial infection may partially disrupt the host cell membrane of the nasopharyngeal orifices, allowing the corona viral naked RNA to enter into cell cytoplasm. The viral genome thereby may multiply within the human cell and cause COVID-19 disease.

Mold hyphae is representative of mechanical vectors that may have cellulose as part of their cell wall, which in addition to physically present fine silica can attract the coronavirus or its naked RNA to stick to it and stay intact for a long time at room temperature. The same thing may happen when coronaviral naked RNA attaches to silica present in dust or dirt in the indoors. Thus, if such a naked RNA is physically integrated with mechanical vectors, it may gain entrance into the nasopharyngeal orifice or buccal cavity, where it can cause disease. Conversely, the injured coronavirus with defective RNA or even partially damaged RNA, after it is introduced into a human cell, may integrate with other virulent coronavirus or co-infecting animal viruses through recombination and become a novel pathogenic virus. Such integration appears likely as the source of H1N1 virus in 1919 and other SARS-CoV, MERS-CoV and SARS-CoV-2 viruses.

Current experience with COVID-19 shows that the disease is more pronounced in people who are in an ICU, evidenced by increased concentration of pro-inflammatory cytokines in their blood versus the levels for people who were not in an ICU. It appears necessary that hospitals take extra precautions to inactivate even the SARS-CoV-2 naked viral RNA in their environment. Hospital rooms must be sanitized periodically to eliminate mechanical vectors that can harbor not only COVID-19 virus but also its naked RNA. Measures must be discovered to inactive not only the intact, damaged, or injured COVID-19 virus, but also naked coronavirus RNA. Countermeasures are needed that can be applied both in households and in public places. In particular, protective measures must eliminate further transmission of SARS-CoV-2 coronavirus not only through direct contact but also through different mechanical vectors into human cells, to cause COVID-19 disease.

It would be desirable to devise a method of inactivating naked RNA from treating spaces outside the human body. To fully achieve this goal, reference to naked RNA must be regarded as including RNA that is exposed in full or in part from the envelope of a virus molecule. The desired method of inactivating the naked RNA must accommodate different degrees of partial coverage by envelope membrane, by lipid molecules, or by other remnants of the virus molecule as well as by environmental debris. For practical utility, the method will be effective to also inactivate non-naked RNA, which might include the RNA within an intact nucleocapsid structure.

It would be desirable to devise a method of inactivating mechanical vectors capable of delivering even a portion of the COVID-19 virus to a human host, from a treating environment outside the host human body.

To achieve the foregoing and other objects and in accordance with the purpose of the present invention, as embodied and broadly described herein, the method and apparatus and method of this invention may comprise the following.

BRIEF SUMMARY OF THE INVENTION

Against the described background, it is therefore a general object of the invention to inactivate naked genetic material such as RNA and DNA of the viruses pathogenic to humans and animals in a contained environment outside the human body.

Another object is to provide effective precursive treatment to consequentially inactivate naked viral genetic material by implementing a multistage treatment regimen against associated agents and substances.

According to the invention, a method, system and apparatus inactivates naked viral genetic material, with RNA being a significant example, and mechanical vectors in treating space external of the human body. For example, in a progressive treatment to reach and inactivate naked RNA as well as full and partial precursors, a detergent effective against membranes with a lipid moiety is formulated and misted throughout a bounded area and then granted a period of repose. This is followed by application of an inactivator of viral spike proteins on any present coronavirus members as well as an inactivator of other residues. Thereafter the threat of RNA transmission is reduced by application of an inhibitor of mold and mechanical vectors, which include yeast and bacteria. The area is treated to receive enzymatic agents, followed by application of enzymes effective against hyphae, acting against associated carbohydrates, cellulose, cell walls, and membranes of yeast and bacteria, which can also act as mechanical vectors. The exposed and prepared RNA and DNA, as present, are finally inactivated by application of RNA-ASE and DNA-ASE enzymes.

The following description discloses preferred embodiments of the present invention and serves to explain the principles of the invention.

BRIEF DESCRIPTION OF THE DRAWINGS

FIG. 1 is a chart of process steps of a Six-Step Treatment with a schematic rendition of apparatus for carrying out the steps.

DETAILED DESCRIPTION OF THE INVENTION

Figure 2:
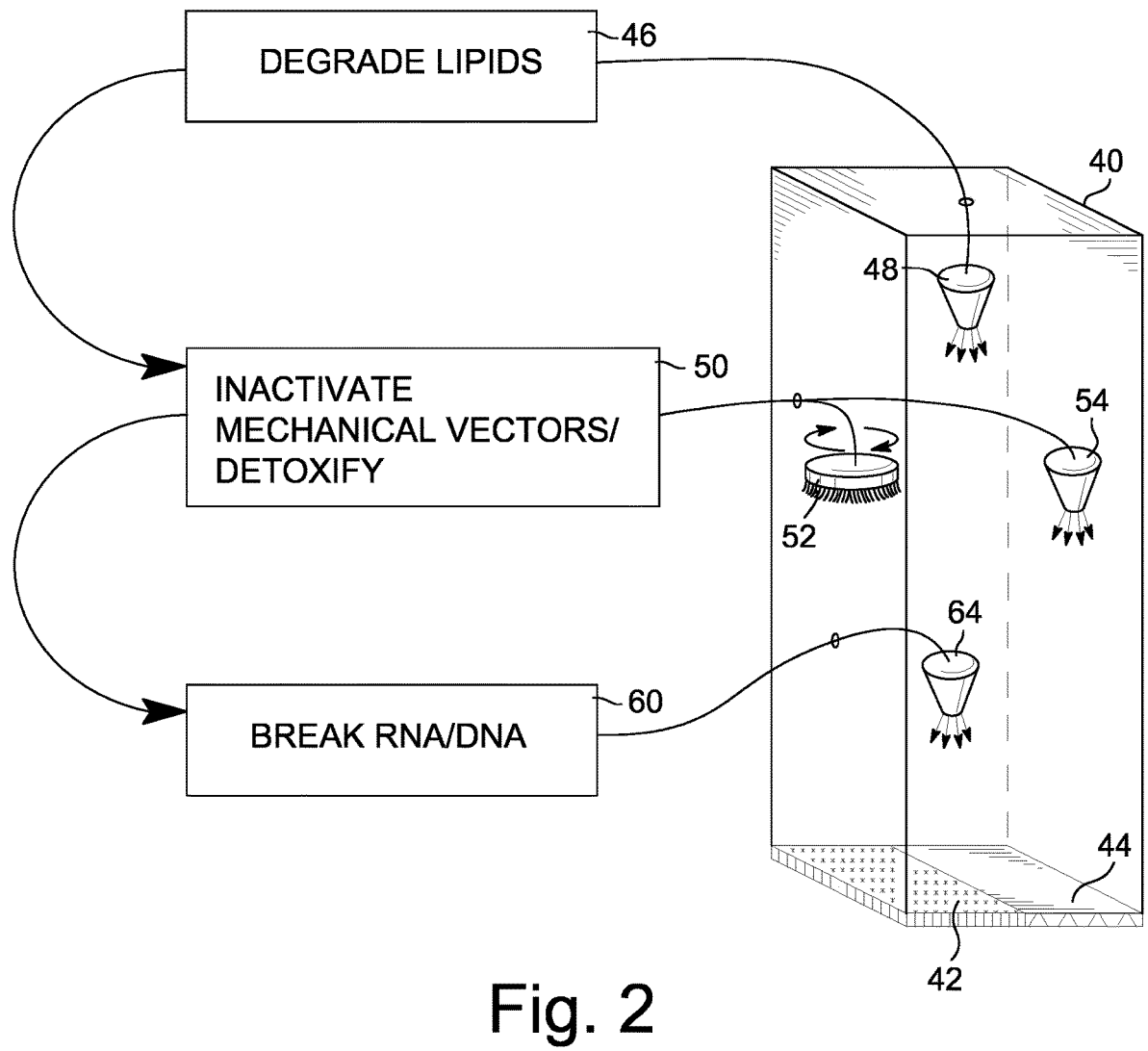
FIG. 2 is a chart of process steps of a Three-Step Treatment with a schematic rendition of apparatus for carrying out the steps.

The invention is a multistage procedure for exposing and inactivating naked viral genetic material that may be found within a bounded area. Naked viral genetic material such as RNA and mechanical carriers effective to transmit the genetic material to a human may be found in a bounded area or environment 10, FIG. 1, outside the human body. The invention is not limited to inactivating coronavirus, but this virus is currently associated with a rapidly spreading disease and is addressed herein for the immediate importance of inactivating it. The conditions leading to naked RNA in the environment are variable. It is difficult to have accurate expectations of circumstances surrounding such RNA, such as whether the RNA is entirely naked, partially covered by residual portions of a lipid-containing envelope of a damaged coronavirus body, or otherwise obscured. A process of treatment has been created that penetrates potentially interfering conditions, including entire or fractional interfering coatings and debris to inactivate RNA. Thus, the process not only inactivates intact, damaged, and injured COVID-19 virus but also all degrees of naked coronavirus RNA.

Host environments 10 for the genetic material, where the treatment can be applied, are generally referred to as defined spaces or treating spaces. Thus, the defined treating space is any area where the treatment is applied, with preferred defined spaces being areas at least partially closed, bounded by walls, so that the treatment can be simultaneously applied throughout the defined space for best effectiveness. Treating spaces need not be sealed. The treatment is effective in the presence of doors, windows, and passageways communicating with the treating space, allowing limited air with external environment.

The treatment can be applied in spaces inclusive of households and public places. Without limitation, the threat of naked RNA infection exists in residential homes and especially in homes-for-sale or for rent, visited by potential new occupants; or sold, rented or otherwise transferred to new occupants or tenants. By way of example and not limitation, host environments for application of the treatment are cars including private cars, rental cars, taxis, and shared ride cars, new and used cars for sale, and loaner cars offered by dealerships. Other host environments for the virus exist in hospitals and emergency care facilities, doctor's waiting rooms and examination rooms, nursing homes, business offices, hotels, hospitality facilities, restaurants, classrooms, airplane cabins, airports, trains, elevators, escalators, cruise ships, and all other public facilities, including but not limited to religious or professional congregations such as churches and convention centers. In hospitals, the pervasive problem of hospital-acquired infections demonstrates a vast unmet need for better control of many types of virus and infectious agents, where the environment 10 represents, without limitation, medical lobbies, hallways, waiting rooms, diagnostic rooms, patient rooms, treatment rooms, operating rooms, and even restrooms. This process eliminates further transmission of SARS-CoV-2 coronavirus through direct contact and also through different mechanical vectors introducing the virus into living human cells to cause COVID-19 disease.

The term "naked" as referring to genetic material such as RNA in a host environment refers such material being at least partially unenclosed from full encapsulation within a viral envelope with lipid molecules. The virus body originating the RNA no longer is entirely intact. The multistage treatment process overcomes numerous potential conditions of the RNA, with one such condition being the presence of a membrane of lipid molecules or nucleocapsid covering some or the entire RNA strand. Nucleocapsid membrane is likely to be present because the intact coronavirus contains the RNA strand in an envelope. If RNA is released to the environment outside of a human host, the envelope may be opened or damaged due to many circumstances whereby sections of the damaged envelope continue to shelter or adhere to the RNA.

Steps for preventing transmission of naked viral genetic material are applied over a treating space outside the human body. This space is variable according to each situation. The following series of steps has been found to be effective with respect to treating RNA as a pertinent example of naked viral genetic material.

A viral envelope degrading step: In a stage of the procedure, an agent degrading to lipids of the RNA viral envelope is formulated and applied to the treating space to rupture, fragment, or otherwise degrade the integrity of any present protective membrane, which typically are remnants of the parent virus body. Examples of a lipid degrading agent are a detergent or polysorbate. The agent can be applied by spraying in the treating space, using a fine mist to penetrate all parts of the environment.

A surface protein inactivating step: The integrity of the virus structure or of residues thereof can be degraded in a further way by formulating and applying an agent that inactivates the surface proteins of a virus body. These proteins are surface structures on the envelope with the lipid moiety and often are prominently shown in images of a coronavirus to have a distinctive T-shape. These are often referred to as spikes, and these spikes are important to the spread of the virus into human hosts because the head of the T-shape can attach the virus to a host cell. An effective method of inactivating spikes, whether on an intact virus body or on a mere fragment still associated with RNA, will reduce or eliminate the ability of the spikes to participate in transmission of the virus to a human host. An effective spike degrading agent can be formulated from chlorine or chlorine derivates and calcium chloride. An effective method of application is to spray the treating space with such a spike inactivator, thereby incapacitating a major transmission method for delivering the virus or a naked RNA fraction thereof to a human host.

A mechanical vector inactivating step: Mechanical vectors potentially can transmit naked RNA to a host. Mechanical vectors often are components of mold, yeast, or bacteria, which may be either alive or dead. An effective mechanical vector inactivating or degrading agent is prepared using an inhibitor effective against entities providing mechanical vectors, such as mold, yeast and bacteria. When the treating space is carpeted or has a fabric surface to be treated, the inhibitor is used either alone or in combination with a shampoo. An antifungal medication can be added to the shampoo. An antibiotic such as natamycin, also known as primaricin, is a suitable antifungal medication to add to the shampoo. When a hard floor surface is being treated, a diluent such as water is added to dissolve the antifungal agent prior to mixing with the mechanical degrading agent, such as a shampoo, and applying it to the hard floor surface. Application by spray is suitable.

A surface detoxifying step: After application of some or all of the previously described treatment agents in the treating space, it is desirable to refresh treated surfaces from previously applied agents to avoid subsequent interference with or neutralizing of further agents to be applied. The detoxifying agents can be enzymatic treatments. Previously applied agents otherwise may be detrimental to ultimately applied enzymes. For example, chlorine or other halogens are to be neutralized or removed. A detoxifying agent is formulated of thiosulfate, which prepares the treating space for the next steps. Also, it is helpful to extract silica, which otherwise remains a transport vector. As an example, thiosulfate agent is sprayed in the treating space and then solids such as silica are removed by suction pick-up.

A reducing step applied to carriers of genetic material such as RNA. An agent is formulated of preparatory enzymes suitable to reduce carrier micro-organisms to smaller units. Carriers of RNA or other genetic material include mold hyphae, yeast, and bacteria. Chosen preparatory enzymes are applied by spray to the treating space. The preparatory enzymes are chosen to be effective to degrade carriers such as starch, remove carbohydrates, disrupt cell walls and membranes, and break cellulose on hyphae. Specific examples of suitable preparatory enzymes are cellulase enzyme and alpha amylase enzyme.

A genetic material inactivating step effective against RNA and DNA. As a tentatively final step, an RNA inactivating agent is prepared and applied by spray to the treating space. After completion of prior steps, the RNA is expected to be available to be contacted and degraded by the inactivating agent, which breaks the RNA strand into smaller components, thereby inactivating the RNA and terminating the potential for spreading the viral disease by naked RNA. An inactivating agent for RNA is variously known as ribonuclease, rna-ase. or RNase. It catalyzes the degradation of RNA. Similarly, an enzyme can be chosen to inactivate naked DNA in the treating space. A suitable inactivating agent for DNA is an enzyme that catalyzes the hydrolysis of DNA into oligonucleotides and smaller molecules. An inactivating agent for DNA is variously known as dna-ase, DNase, or deoxyribonuclease. The DNA inactivating agent is applied by spray in the treating space and breaks the strands of naked DNA that are present. A combination of RNA-ase and DNA-ase can be sprayed, as well.

SIX-STEP TREATMENT—Referring to FIG. 1 of the drawings as a specific example for the purpose of illustration but without limitation, the multistage procedure may be carried out in the following six steps.

In a first step 12, FIG. 1, an agent effective against viral membranes with lipid molecules is applied in the treating space 10. According to a preferred formulation, a household or industrial detergent is obtained or prepared in reference quantity of 1000 ml. Suggested ingredients are some or all of denatured alcohol (QS), alkyl dimethylamine (QS), sodium laureth sulfate (QS), phenoxy ethanol (QS), other flavor ingredients (QS), and other adjunct major or minor detergent functional ingredients (QS). To this indicated volume, desirable additions are some or all of 0.1 to 1.0% polysorbate-60 (1 ml to 10 ml or grams/liter of detergent), plus 0.1 to 5.0% sodium bicarbonate (1 gram to 50 grams/liter of detergent), plus 0.01 to 0.25% calcium chloride (0.1 gram to 2.5 grams/liter of detergent).

As required, the detergent volume is diluted with water or any soluble liquid so that it can be easily sprayed as a fine mist. The detergent is sprayed as the fine mist using a fine nozzle spray head 14 to reach all the areas of a treating space 10, FIG. 1. By example and not limitation, the treating space 10 often is a room, hallway, vehicle cabin, or building. The sprayed mist is allowed to settle for a sufficient variable time allowance, often 5 to 30 minutes.

In a second step 16, an inactivator of spike proteins is applied. After all the sprayed liquid from step one has settled, a spray head 18 is used to apply the inactivator solution. A suggested composition is some or all of 10 to 100 parts per million chlorine solution or its derivatives such as chlorine dioxide or other related halogens and their derivatives, such as bromine and iodine, and 0.0001 to 0.01% calcium chloride. After application, the sprayed solution is allowed to settle for a minimum of 5 to 10 minutes before proceeding with step 3.

In a third step 20, an agent is applied to inactivate mechanical vectors. Where carpet or similar floor covering is present, the carpet 21 is shampooed using a carpet shampoo brush 22 or other type of carpet shampoo equipment, optionally using commercial carpet shampoo as a base. Suggested additions are some or all of 0.1 to 1.0% polysorbate-60 (final percentage in shampoo) or any other nontoxic polysorbate, chlorine or other related halogens to end up with a concentration in the shampoo of 5 to 50 parts per million of chlorine or other related halogen. Suggested further additions are some or all of sodium propionate added to arrive at a concentration of 0.05 to 0.5% in the shampoo, natamycin added to arrive at a concentration of 0.0001 to 0.02% in the shampoo, and hydrogen peroxide added to arrive at a concentration of 0.1 to 3% in the shampoo. Any other all natural antimycotics and/or microbial inhibitors may be added into the shampoo. After completing the shampooing of the carpet 21, it is allowed to dry for between a few minutes to an hour, or as required according to monitoring and analysis of the location, determined, for example, by thickness of the carpet.

If the treating area 10 does not have carpet 21 and instead has a bare floor 23 such as hardwood, granite, marble, vinyl, or bare cement flooring, the third step procedure is modified by using a more suitable inhibiting solution. A suggested composition is some or all of a mild commercial or formulated liquid detergent or a dilute detergent (such as water with the inclusion of a small amount of detergent) along with the following ingredients: 0.1 to 1.0 percent polysorbate-60 (final percentage in solution); chlorine, chlorine derivative ingredients, or other related halogens to end up with a 5 to 50 parts per million chlorine; or sodium propionate to arrive at 0.05 to 0.5% in the solution; natamycin to arrive at 0.0001 to 0.02 percent in the solution; and hydrogen peroxide to arrive at 0.1 to 3 percent in the solution. Any other all natural antimycotics and/or microbial inhibitors may be added into the solution. Then, the solution can be sprayed onto the bare floor 23 and allowed to dry for from few minutes to an hour, or as required according to conditions, such as the composition of the flooring material.

In a fourth step 24, the treating space 10 is treated with a detoxifying solution to prepare space 10 to receive enzymatic agents. A suggested procedure is to use a spray head 26 to spray 0.05 to 0.2% solution of sodium thiosulfate on carpet 21 to detoxify the residual chlorine. Allow 5 to 30 minutes for this solution to act. Then using a suction head 28 or other type of carpet vacuum equipment, vacuum the carpet 21 to remove solid residues and any loose silica particles. If the room has no carpet but has a bare or hard floor 23 as further described above, spray the solution via head 26 to detoxify chlorine, and then sweep or vacuum the floor after 5 to 30 minutes of applying the solution.

In a fifth step 30, a carrier reducing agent is applied to space 10 to reduce carriers to simpler units. An enzymatic agent reduces the carrying capacity of RNA carriers and thereby shortens the life of naked RNA that otherwise sticks to and gains benefit from attachment to the carriers. In particular, genetic material carriers are micro-organisms such as cellulose and starch, which often are present either as an integral part of mold hyphae or loosely lying in the treating space 10. These genetic material carriers are reduced to simpler units that are less suited to carry genetic material such as RNA. Enzymes are applied that digest the carriers, reducing the larger carriers to fragments as small as glucose molecules or short glucose chains. The fragments and discarded RNA become easier to further individually treat and remove, such as by vacuum sweeping with a head 28. A suggested enzyme solution is prepared in chlorine-free water (preferably distilled water or RO water):

a. Cellulase enzyme—0.005 to 0.01%; and
   b. Alpha amylase enzyme—0.0005 to 0.005%.

Where a carpet 21 is being treated, a spray head 32 is used to spray the prepared solution on the carpet. Where a bare floor or hard floor 23 is being treated, spray head 33 is used to spray the prepared solution on the bare floor. Following treatment, a suggested drying period is 5 to 15 minutes or as required according to monitoring and analysis before proceeding with the sixth step.

In a sixth step 34, enzyme solutions are prepared and applied to break and inactivate RNA and DNA. A suggested procedure is to apply a solution of RNA breaking enzyme with a protective agent, which is effective as a yeast and mold inhibitor that protects the RNA breaking enzyme. The RNA breaking enzyme may be supplied as a solution of 0.01 to 0.1% RNA breaking enzyme (RNA-ASE). The protective agent may be one or more antimycotics and microbial inhibitors chosen from the group consisting of a solution of 0.0001 to 0.01% natamycin, 0.01 to 1.0% sodium propionate, 0.05 to 0.3% sorbic acid, or combinations thereof. The antimycotic and microbial inhibitors are preferred to be derived from natural sources.

Within the sixth step, a DNA breaking enzyme may be applied in combination with a protective agent effective as a yeast and mold inhibitor that also protects the DNA breaking enzyme. The DNA breaking enzyme may be supplied as a solution of 0.001 to 0.01% DNA breaking enzyme (DNA-ASE). The protective agent may be one or more antimycotics and microbial inhibitors chosen from the group consisting of a solution of 0.0001 to 0.01% natamycin, 0.01 to 1.0% sodium propionate, 0.05 to 0.3% sorbic acid, or combinations thereof. The antimycotic and microbial inhibitors are preferred to be derived from natural sources.

With carpeted surfaces in space 10, the spray head 36 may be used to apply the enzyme solution and protective solution by spraying the two solutions on all surfaces of the space 10 including both air space and floor 21. With bare or hard floors in space 10, spray head 37 is used to treat the floors by using nozzles 36, 37 suitable to spray a fine mist. The mist is allowed time to settle. As an alternative to the aforementioned two solutions, the spray may employ an enzyme solution of preferably all-natural RNA-ASE and DNA-ASE enzymes. Such enzymes can be obtained as cell lysates, and extracellular and intracellular nucleases belonging to beneficial micro-organisms, along with their growth end products such as immunomodulins.

Periodically repeat the procedure to inactive the naked RNA of the coronavirus and the mechanical carriers such as live-or-dead mold hyphae, other silica varieties, or mechanical vectors. This procedure is particularly necessary to curb the spread of COVID-19 coronavirus in treating spaces where one or more new persons or new groups follow the presence of an earlier person or group. The health condition of the predecessors can lead to residual, long lasting exposure of the new occupants to coronavirus through residual, naked RNA.

THREE-STEP TREATMENT—With reference to FIG. 2, a condensed or revised process has been developed to inactivate naked RNA, and also effective to inactivate naked DNA, in a treating spaced outside the human body. This shortened process employs three steps, effective but not limited to periodic usage after initially treating a space using the Six-Step Treatment, to both inactivate naked RNA and inactivate mechanical vectors that otherwise could assist naked RNA in entering the human body to cause COVID-19 infection.

A first step 40 in the Three-Step Treatment is a preparation and application of a detergent effective against viral membranes with lipid molecules. A suitable example is to prepare 1000 ml of detergent. A suitable detergent may be of a household or industrial type, and hence may be commercially formulated or custom formulated. It is desirable for the detergent to contain denatured alcohol (QS), alkyl dimethylamine (QS), sodium laureth sulphate (QS), flavor ingredients (QS), and other adjuvant major or minor detergent functional ingredients (QS). To the selected or prepared detergent, the efficacy of the formulation is improved by addition of 7.5 grams of plysorbate-60 (0.75%), 37.5 grams of sodium bicarbonate (3.75%), 1.0 gram of calcium chloride, and 2 ml of 6% chlorine solution (120 ppm). Application is by spraying the solution into the air within the treating space and making sure all other corners of the space are covered. The spray is applied using a spray head 48 with a nozzle. The spray also is applied to both carpets 42 and bare floor surfaces 44. After application, the sprayed solution is allowed to settle. Fifteen minutes is an effective settling time.

A second step 50 in the Three Step Treatment is directed to inactivating mechanical vectors and detoxifying surface and preparing the treating space 10 for subsequent application of enzymes. A carpet shampoo, which may be either commercially sourced or custom formulated, is enhanced by addition of polysorbate-60 to arrive at 1% in the shampoo. The shampoo is further enhanced by addition of 0.5% sodium propionate, 0001% natamycin, and hydrogen peroxide to arrive at 3%. As additional enhancing agents, 0.3% sorbic acid or potassium sorbate and 0.05% sodium thiosulphate are added. As thus modified, the shampoo is applied by suitable means such as a brush head 52 to a carpet 42 or a spray head 54 to a bare floor 44 and allowed to dry.

A third and final step 60 in the Three-Step Treatment is application of RNA and DNA degraders. RNase is an enzyme that promotes the breakdown of RNA into oligonucleotides and smaller molecules. DNase performs similarly to degrade DNA. This third step is to prepare a solution of an enzyme degrading agent of water in quantity of 1000 ml or as required, catalase added to a final concentration of 0.005%, cellulase added to a final concentration of 0.01%, and alpha amylase added to concentration of 0.005%. RNase is added to arrive at a final concentration of 0.002%, DNase is added in concentration of 0.0001%, sodium propionate is added in a concentration of 1.0%, natamycin is added in a concentration of 0.01%, and sorbic acid is added to a concentration of 0.15%. Quantities of all listed additions are adjusted to arrive at the indicated final percentages concentration in the solution. Using a spray head 64, the resulting solution is sprayed on the entire surface of the treating space 10 including on any carpet 42.

Time periods have been determined, depending upon the application site and space, to reapply the process to a variety of treating spaces 10 in order to have reliable, continuous inactivation of naked RNA and its transport vectors. According to the type of treating space, the process should be repeated at least as follows: hospitals—every time a patient is transferred out of a space, before a new patient is transferred in; operation theaters and other hospital facilities—daily, hotel rooms—revised steps 1 and 3 daily, all three steps once per week; restaurants—revised steps 1 and 3 daily, all three steps once per week; residential houses—once each three months; offices—once per week; passenger aircraft—once per week; passenger buses—once per day; military barracks—twice per week; movie theaters—once per day; sports arena—once per week and prior to a game; churches—once a week: manufacturing facilities—once per day, at the end of operations; and airports—once per day. In treating spaces 10 without carpeting, the frequency of treatment can be selected according to the tolerance of the flooring material. With respect to the entire list, the frequency of treatment should be adjusted upward when known instances of the virus are present.

A test procedure has been developed to evaluate the efficacy of the system using a count of microscopic mold hyphae. According to the test procedure:

Prepare a solution of 0.5% sorbic acid and dispense into two test tubes in 10 ml quantities. Using the first test tube, place a first sterile cotton swab into the solution in the test tube. Prior to the treatment, use the first swab impregnated with the above solution to swab a chosen or suspected area of the treating space 10 and place the used first swab into the solution in the first test tube. Designate this first test tube as sample "A," prior to treatment of space 10. After treating space 10, use the second test tube with a fresh, second cotton swab, to swab a test area of space 10 follow the same procedure, designating the second test tube as sample "B." In the laboratory, fix the samples A and B onto microscope slides using gentle flame and then stain them with methylene blue solution for 1 to 3 minutes. After staining, wash off the methylene blue dye, and examine the slides under microscope using an oil immersion lens. Less than 10 hyphae or mold cells under microscope are considered as best and the cleaning is considered to be thorough, which indicates that the mechanical vectors have been dismantled. A comparison of before-and-after treatment (microscopically) gives the efficiency of the procedure of the current invention since mold hyphae have been elected as indicator.

The invention is effective to prevent nosocomial infections. These hospital acquired infections or health-care-associated infections are due to multiple antibiotic resistant bacteria such as methicillin-resistant *Staphylococcus aureus* (MRSA), *Clostridium difficile* (C. diff), *Pseudomonas aeruginosa, Acinetobacter baumannii, Klebsiella pneumoniae, Stenotrophomonas maltophilia*, members of the carbapenem-resistant Enterobacteriaceae, enteropathogenic *Escherichia coli* (EPEC) and certain strains of *Enterococcus faecium*. The most notable nosocomial yeast infection of record was caused by *Candida albicans*. In addition, several viral and fungal pathogens are involved in hospital acquired infections. The following pathogenic mold species are involved as causative factors in nosocomial infections: *Aspergillus, Fusarium*, Mucorales and *Scedosporium*. The following viruses are categorized as causative agents for hospital acquired infections: respiratory syncytial virus, Varicella zoster virus, influenza virus, adenovius, parainfluenza, and rubeola virus. The recent, SARS-CoV-2 can be included in this list, since it is highly prevalent in the hospital atmosphere due to hospitalization of COVID-19 patients in large numbers. The most common types of nosocomial infections are associated with or cause blood stream infections (BSI), pneumonia (ventilator-associated pneumonia (VAP)), surgical site infections (SSI), urinary tract infections (UTI), and gastro-intestinal tract infections. It has been reported that hospitalized COVID-19 patients may be developing nosocomial infections due to contaminated hospital equipment such as ventilators and surroundings.

As described, nosocomial infections can be caused by multiple antibiotic resistant pathogenic bacteria, pathogenic molds, pathogenic yeasts, and pathogenic viruses. An all-too-common experience is for a patient to visit a health care facility for treatment of a specific disease. While being treated for the specific disease, the patient develops a new, nosocomial disease that originates from the visit to the health care facility. According to CDC, these hospitals acquired infections are now turning into community associated infections with a 50% death rate of the infected people. In other words, these infections are migrating from the hospital environment to mainstream communities. Perhaps hospitals are a source of spreading COVID-19 infection. Thus, hospitals, health care facilities and doctors' offices must take extra precautions to absolutely destroy or kill these hospital-associated infection-causing, pathogenic micro-organisms, to prevent the spread of potentially fatal diseases and avoid contributing to pandemics.

The present invention, including methodology, destroys the intact coronavirus and its naked RNA that causes COVID-19 disease. The invention also inactivates or kills the carriers of coronavirus and/or their naked RNA. The carriers include live or dead molds, yeasts, and bacteria, including most or all of the microbial origin etiological factors involved in hospital acquired infections.

The Three-Step Treatment and the Six-step treatment were tested for efficacy in inactivating naked virus. For purposes of this evaluation, the naked virus was simulated by substituting samples of *Streptococcus thermophilus* and its bacteriophage. It may be recalled that both "bacteriophage" and "virus" refer to a virus and to some extent can be interchanged. A "bacteriophage" or "phage" is the more limited term, referring to a virus that infects bacteria. Experiments were conducted to evaluate the success in inactivating both the substitute virus and substitute naked genetic material. As a further safety consideration, experiments involving genetic material employed naked DNA rather than naked RNA. It was considered that testing by using real naked RNA, specifically of the corona virus SARS CoV-2, is potentially too dangerous, while testing with naked DNA belonging to a bacterial virus (bactriophage) affecting a non-pathogenic, food grade bacteria, is safer while producing a similarly indicative result.

Experiment 1. A first sample of 100 ml of sterile 10% solids reconstituted nonfat dry milk was sterilized by autoclaving at 121° C. for 15 min. *Streptococcus thermophilus* bacteria was inoculated at 1% level into the sterilized milk, forming a first inoculated milk culture. The first inoculated milk culture was incubated at 37° C. for 12 hours, forming a positive control.

Separately, a second sample of the milk was incubated with a 1% inoculum of *Streptococcus thermophilus* bacteria and it's specific bacteriophage, forming a second inoculated milk culture. The second milk culture also was incubated at 37° C. for 12 hours.

At the end of the 12 hr. incubations, pH measurements were taken on both the first and second cultures. The first milk culture registered pH of 4.3, indicating that the first milk culture was very active. In contrast, the second milk culture registered a pH of 6.0, indicating that the *Streptococcus thermophilus* bacteria were killed by its bacterial virus, the bacteriophage. The second milk culture was assayed for a virus count. The virus count was $220 \times 10^7$/ml, whereas the bacteria count in the same second milk culture was <100/ml, indicating that the bacteria was killed by the bacteriophage. The first milk culture—the control having no virus—had a bacteria count of $267 \times 10^7$ bacteria/ml.

To determine the virus count in the second milk culture, containing both bacteria and virus, the second milk culture was treated using 0.5 ml of chloroform/10 ml, thereby inactivating any residual bacteria, but not the virus, thus forming a preparation of virus. This preparation of virus was sprayed in quantity of 0.1 ml onto a strip of sterile carpet sized 2×2 inches, thereby forming virus-impregnated carpet. An initial virus count was taken by swabbing the virus-impregnated carpet, and placing the swab into 10 ml sterile buffer solution. The virus count for the virus-impregnated carpet was $35 \times 10^4$ ml (350,000 virus particles).

The same virus impregnated carpet was then treated using the above-proposed treatment with chloroform to inactivate the virus. After the treatment, the total virus count was determined by swabbing the carpet with buffer impregnated swab. The 10 ml of buffer solution with swab was treated using 0.5 ml of chloroform to inactivate any contaminating bacteria acquired from dipping the virus-impregnated carpet sample into the buffer, thereby forming a virus-inactivated buffer solution. The post-treatment virus count of the virus-impregnated carpet was <10/ml of the virus count for the virus-inactivated buffer solution, indicating that the virus on the virus-impregnated carpet was totally inactivated by use of the Three-Step Treatment. Similar results were achieved with the Six-Step Treatment under the same laboratory conditions.

Experiment 2. An experiment was conducted to determine whether the virus on the impregnated carpet was totally inactivated. The virus-impregnated carpet, after the proposed Three Step Treatment, was swabbed and inoculated into 100 ml of sterile reconstituted 10 percent solids non fat dry milk containing the *Streptococcus thermophilus* bacteria (the substitute host). As before, the first inoculated milk culture served as control. Both first and second milk cultures were incubated at 37° C. for 12 hours. The pH of both was measured and evaluated as an indirect indicator of growth. The pH of the control culture, which had been inoculated with only bacteria, and the pH of the second milk culture, which was under test for virus content, both registered pH as 4.8, indicating that the virus was totally inactivated using the Three-Step Treatment. Microscopy also revealed that the bacteria were not affected by the inactivated virus preparation. The bacteria counts of the two samples were at $250 \times 10^7$/ml for the control and $270 \times 10^7$/ml with the inactivated bacteriophage, indicating that due to inactivation rendered by use of the Three-Step Treatment, the virus was not effective in killing the bacteria. The viral counts were <10/ml in the sample of culture medium inoculated with both the bacteria and the virus-inactivated buffer solution, further confirming that use of the Three-Step Treatment has totally inactivated the virus, similar to the Six Step Treatment.

Experiment 3. An experiment was conducted to study whether naked viral DNA can infect and multiply in heat damaged (cell wall injured) *Streptococcus thermophilus* bacteria. This experiment is designed to mimic the effect of naked RNA of coronavirus or other DNA virus infecting a damaged or injured human cell, as in the case with some comorbid conditions.

A crude naked viral DNA was prepared by using the following procedure. A bacteriophage active against *Streptococcus thermophilus* was prepared using the procedure outlined in Experiment 1. A sample with bacteriophage was prepared without any residual bacteria by treating the sample of this viral preparation with chloroform, as outlined in Experiment 1. The chloroform was driven out of the sample with aeration by bubbling sterile air into the viral preparation. A virus count was determined using a plaque assay. The virus count was $680 \times 10^7$/ml. The *Streptococcus thermophilus* bacteriophage has both a head and a tail with a tough, significantly heat resistant protein coat. In order to destroy the protein coat enclosing the viral DNA, liquid chlorine was added to 10 ml of the viral preparation to arrive at a final concentration of 100 ppm. The sample was thoroughly shaken for approximately one minute to denature the viral protein coat. Immediately thereafter, 1 ml of 10% solution of sodium thiosulphate was added to the viral preparation to inactivate the chlorine. A viral count was conducted using a plaque assay to check for viability. The viral count was <10/ml indicating that the experimental procedure had inactivated the virus particle. Due to denaturation of the head and tail protein coats, the inactivated virus particles could not infect a host, here represented by live *Streptococcus thermophilus* bacteria. This inactivation is attributed to destruction of the protein shell of the bacteriophage viral protein on both the head and tail. Thus, adsorption of viral particles to infect the *Streptococcus thermophilus* bacteria had been hampered. This conclusion does not go so far as to say that the DNA inside the bacteriophage particle is inactivated. The sample was vigorously shaken, homogenized and sonicated to free the crude viral DNA from the bacteriophage particle. This sample will be regarded as naked DNA.

Experiment 4. An experiment was conducted to determine the viability of genetic material introduced into a host cell. DNA can be available for introduction if naked or if it has not been inactivated by a prior treatment with chlorine. The viability can be tested by introducing the naked DNA into an injured host cell, represented by an injured bacteria cell, to determine whether the DNA produces active virus particles.

Injured bacteria, representing host cells, were prepared by applying heat. A mixture was prepared by using 10 ml of fully grown *Streptococcus thermophilus* bacteria culture with 2% sodium chloride. The mixture was heat treated to 145° F. and held at that temperature for 10 min. to form a heat treated culture. The heat treated culture was cooled and plated to determine a live bacterial count, using tryptic soy agar. The bacteria count before heat treatment was $100 \times 10^6$/ml. After heat treatment, the bacteria count was <10/ml, indicating that the bacteria of the heat treated culture indeed had been heat-injured. This heat treated culture was inoculated into sterile 10% solids reconstructed nonfat dry milk, with and without addition of the naked DNA virus preparation. The samples were incubated at 37° C. for 12 hours. The pHs of both preparations were determined at the end of the incubation. The heat-injured *Streptococcus thermophilus* (host) had pH 5.5, whereas the heat-injured *thermophilus* with the viral naked DNA had pH 5.9, indicating that naked DNA introduced through the damaged cell walls of the bacteria was still able to infect the bacteria to make viral progeny. Although the concentration of virus particles was significantly low, i.e. 200/ml, this experiment demonstrated that naked DNA can infect injured bacteria cells and can multiply. However, when the proposed Three-Step Treatment was applied to the virus and then applied to the heat-injured bacteria cells, the naked DNA of the bacteriophage was totally inactivated, as demonstrated by the fact that the bacteriophage did not replicate in the heat-injured bacteria cells. It may be concluded that the Three-Step Treatment also is effective to inactivate both the virus and its naked genetic material, as indicated by the Six Step Treatment.

As further confirmation of effectiveness, the laboratory room where the experiments were conducted using both the Three-Step Treatment and Six Step Treatment was tested for the presence of SARS-CoV-2 virus RNA, using the RT-PCR test and using surface test procedures suited for metal and granite surfaces. Further, none of the employees who worked in the treated laboratory facility contracted SARS-CoV-2 infection, conforming to the evidence that both the Three-Step Treatment and Six Step Treatment are effective to inactivate both the virus and its genetic material.

Experiment 5. An experiment was conducted using both live and dead transport vectors to evaluate interaction with both DNA virus and naked DNA. The evaluation considered interaction with both healthy and heat injured host bacteria. *Penicillium roqueforti* mold provided the transport vectors. The experiment showed that both live and dead transport vectors can harbor both the viruses and the naked genetic material.

Experiment 6. An experiment was conducted to determine the ability of the Six-Step Treatment to inactivate certain household yeast, molds, and bacteria as markers to indirectly determine the efficacy of the treatment to inactivate corona virus and its naked RNA. An additional purpose of the experiment was to inactivate mechanical vectors. According to a test protocol, yeast, molds, and *Enterococcus* bacteria were used as indicators to verify inactivation of corona virus and its naked RNA. According to the experimental procedure, test substrates consisting of small strips of carpet of different colors and texture were sprayed using yeast, mold, and a bacteria-impregnated solution. Initial counts of the yeast and mold were determined by smears applied to dried potato dextrose agar, and an initial count of the bacteria was determined by smears applied to KF *Streptococcus* agar to determine a count of *Enterococcus* bacteria (*Streptococcus durans*). A selection of one-half of the carpet strips was chosen to serve as control and was not treated with the Six-Step Treatment. This one-half of the carpet strips was enclosed in a tough plastic strip.

The remaining one-half of the carpet strips was treated with the Six-Step Treatment. After 48 hours, counts of the yeast, mold, and bacteria were determined by swabbing all of the carpet strips, including controls, using sterile phosphate buffer. The liquid swab was then streaked or smeared onto selective media and incubated at 37° C. After an additional 48 hours of incubation, a count of *Enterococcus* was taken, and after 96 hours at room temperature a count of yeast and mold was taken. These counts of yeast, mold, and *Enterococcus* bacteria are presented in Table 1.

In addition, different color carpets were inspected for color and smell variations due to treatment, compared to the control. Evaluating both the carpet strips as well as a carpeted room, it was confirmed that the Six-Step Treatment neither altered the carpet color nor induced foreign smells. In addition, microscopy of the swabs of both control strips and test strips, dipped in 0.3% potassium sorbate solution, revealed that the Six-Step Treatment significantly reduced the chain lengths of molds and reduced the sizes of yeast cells, indicating that the Six-Step Treatment is effective in killing and digesting mechanical vectors. Methylene blue stain can be used to determine cell injury, as healthy cells take the stain better, showing an intense blue, while dead cells show a faint blue. Applying methylene blue to the solution revealed the lighter color, indicative of dead *Streptococcus durans* bacteria, thereby indicating disruption of the cells and their cytoplasm.

TABLE 1

An indirect showing of effectiveness of the Six-Step Treatment applied to coronavirus and corona virus RNA, determined by using yeast, molds, and *enterococcus* bacterial culture as indicators.

| Carpet Sample a* b* | Yeast and Mold count before treatment c* | Yeast and Mold count after treatment c* | *Enterococcus* bacteria count before treatment | *Enterococcus* bacteria count after treatment d* |
|---|---|---|---|---|
| 1 | 120 | <10 | 272 | <10 |
| 2 | 90 | <10 | 225 | <10 |
| 3 | 130 | <10 | 298 | <10 |
| 4 | 120 | <10 | 218 | <10 |
| 5 | 150 | <10 | 227 | <10 | a. No discoloration of carpet was observed before and after treatment
b. No off odors were detected before and after treatment
c. Chain lengths of molds were significantly reduced after treatment compared to before treatment
d. The indicator bacteria did not pick up the methylene blue stain indicating that the bacterial cell is damaged and killed in comparison to control.

The results of Experiment 6 indirectly show that the Six-Step Treatment is effective to inactivate COVID-19, shown by the use of yeast, molds, and bacteria as indicators. The results suggest positive effect in inactivating the corona viral particles, their naked RNA, and also mechanical vectors that can harbor viral RNA.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention.

What is claimed is:

1. A method of inactivating the infective ability of naked viral genetic material of a coronavirus located within a treating space outside the human body by an ordered sequence of multiple steps, comprising:
 contacting said naked viral genetic material with a lipid molecule degrading agent effective to degrade viral envelope membrane associated therewith, where present;
 contacting the naked viral genetic material with a viral surface spike protein inactivating agent effective to inactivate viral surface spike proteins associated therewith, where present;
 preventing delivery of the naked viral genetic material from said treating space to a host through physical integration with a mechanical vector having capability to deliver the naked viral genetic material to said host by applying to said treating space a mechanical vector inactivating agent in quantity sufficient to inactivate entities providing mechanical vectors, where present, said mechanical vector inactivating agent comprising 0.1 to 1.0% polysorbate-60 and chlorine at concentration of 5 to 50 parts per million of chlorine solution;
 applying to the treating space a surface detoxifying agent in quantity sufficient to inactivate substances detrimental to enzymes that break the naked viral genetic material, where present;
 applying to the treating space a carrier reducing agent, effective to reduce the carrying capacity for genetic material of carrier micro-organisms, where present; and
 inactivating the infective ability of the naked viral genetic material by contacting the naked viral genetic material with an agent effective to inactivate the infective ability of the naked viral genetic material by breaking the naked viral genetic material into smaller components.

2. The method of claim 1, wherein said mechanical vector inactivating agent comprises: shampoo containing 0.1 to 3% hydrogen peroxide and 0.05 to 0.5% sorbic acid.

3. The method of claim 1, wherein said naked viral genetic material comprises: RNA; and said naked viral genetic material-inactivating agent comprises: RNA-ase enzyme.

4. A method of inactivating the infective ability of naked viral genetic material of a coronavirus located within a treating space outside the human body by an ordered sequence of multiple steps, comprising:
 contacting the naked viral genetic material with a lipid molecule degrading agent effective to degrade viral envelope membrane associated therewith, where present;
 applying to said treating space an agent inactivating mechanical vectors and detoxifying surfaces of substances detrimental to enzymes, where present, said agent inactivating mechanical vectors comprising 0.1 to 1.0% polysorbate-60 and 5 to 50 ppm chlorine solution; and
 inactivating the infective ability of the naked viral genetic material by contacting the naked viral genetic material with an agent effective to inactivate the infective ability of the naked viral genetic material by breaking the naked viral genetic material into smaller components.

5. The method of claim 4, wherein said lipid molecule degrading agent comprises: detergent containing 0.75% polysorbate-60 and 3.75% sodium bicarbonate.

6. The method of claim 4, wherein said naked viral genetic material comprises RNA; and said naked viral genetic material-inactivating agent comprises RNA-ase enzyme.

7. The method of claim 4, wherein said naked viral genetic material comprises RNA; and said naked viral genetic material-inactivating agent comprises RNA-ase enzyme, obtained as natural microbial lysates of beneficial micro-organisms.

* * * * *